United States Patent [19]
Power et al.

[11] Patent Number: 5,883,296
[45] Date of Patent: Mar. 16, 1999

[54] PREPARATION OF TETRAKIS (DIHYDROCARBYLAMINO)PHOSPHONIUM HALIDE

[75] Inventors: John M. Power; Bruce C. Berris; David A. Caillet, all of Baton Rouge, La.

[73] Assignee: Albermale Corporation, Richmond, Va.

[21] Appl. No.: 801,051

[22] Filed: Feb. 14, 1997

[51] Int. Cl.⁶ .................................. C07F 9/02; C07F 9/22
[52] U.S. Cl. ................................................. 564/12; 556/13
[58] Field of Search .................................. 564/12; 556/13

[56] References Cited

PUBLICATIONS

Koidan, Marchenko, Kudryavtsev, and Pinchuk, *Zh. Obshch. Khim.*, 1982, 52, 2001.

Primary Examiner—Shailendra Kumar
Attorney, Agent, or Firm—Philip M. Pippenger

[57] ABSTRACT

A mixture is made from (i) a tris(dihydrocarbylamino) phosphoroamidite and/or a hydrohalide thereof, (ii) a strong base (e.g., NaOH) in proportions of about 2.0 to about 4.0 moles of (ii) per mole of (i), and (iii) at least one solvent for the base (e.g., $H_2O$). To this mixture is added a hydrocarbyl monohalide (e.g., EtBr) in proportions of about 1.0 to about 3.0 moles per mole of phosphoroamidite used in forming the initial mixture, and the resultant reaction produces tetrakis (dihydrocarbylamino)phosphonium halide. The process enables more efficient production of tetrakis (dihydrocarbylamino)phosphonium halides, and is capable of being effectively used in large scale production facilities while satisfying the economic constraints of commercial operations.

13 Claims, No Drawings

PREPARATION OF TETRAKIS (DIHYDROCARBYLAMINO)PHOSPHONIUM HALIDE

TECHNICAL FIELD

This invention relates to the synthesis of tetrakis (dihydrocarbylamino)phosphonium halides in which the halogen atom is other than fluorine.

BACKGROUND

As described more fully in now commonly-owned copending U.S. application Ser. No. [Case OR-7006], filed Nov. 22, 1996, tetrakis(dihydrocarbylamino)phosphonium halides are useful as catalysts in halogen exchange reactions between alkali metal fluorides, such as KF, and chloro- and bromoaromatics, such as hexachlorobenzene. A variety of useful fluorinated aromatic compounds can be produced in this manner.

A laboratory synthesis method for the preparation of tetrakis(dihydrocarbylamino)phosphonium halides, is described by Koidan, Marchenko, Kudryavtsev, and Pinchuk, *Zh. Obshch. Khim.*, 1982, 52, 2001, an English language translation of which is available from Plenum Publishing Corporation.

Another prior process to form a tetrakis(dialkylamino) phosphonium halide involves the reaction of tris (dialkylamino)phosphoroamidite with one equivalent of an alkyl halide. The reported yield of the tetrakis(dialkylamino) phosphonium halide was 38.5%. In addition, this prior process involved forming the tetrakis(dialkylamino) phosphonium halide in two stages in separate reactors. The first stage involved reacting a tris(dialkylamino) phosphoroamidite hydrochloride with a small excess of sodium hydroxide to free the phosphoroamidite of the hydrogen chloride. After working up this reaction mixture, the HCl-free tris(dialkylamino)phosphoroamidite was isolated and then subjected in the second reactor to the foregoing reaction with one equivalent of the alkyl halide.

A need exists for a process enabling more efficient production of tetrakis(dihydrocarbylamino)phosphonium halides, especially if the process is capable of being effectively used in large scale production facilities while satisfying the economic constraints of commercial operations. This invention is deemed to satisfy these objectives.

SUMMARY OF THE INVENTION

A process for preparing tetrakis(dihydrocarbylamino) phosphonium halide has been discovered that can produce the product in yields of at least 60%. The process, which is readily adapted for large scale production operations while at the same time meeting cost constraints, comprises:

a) forming a mixture from (i) at least one tris (dihydrocarbylamino) phosphoroamidite and/or hydrohalide thereof, (ii) at least one strong base in proportions of about 2.0 to about 4.0 moles of (ii) per mole of (i), and (iii) at least one solvent for the strong base;

b) mixing with the mixture so formed, (iv) at least one hydrocarbyl monohalide (chloride, bromide or iodide) in proportions of about 1.0 to about 3.0 moles of (iv) per mole of (i) used in forming the mixture of a); and c) maintaining the mixture formed in b) at one or more temperatures at which tetrakis(dihydrocarbylamino) phosphonium halide is produced. Other embodiments and features of this invention will become still further apparent from the ensuing description and appended claims.

DETAILED DESCRIPTION

The phosphoroamidites and phosphoroamidite hydrohalides used in the process have the respective formulas

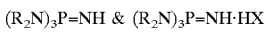

$(R_2N)_3P=NH$ & $(R_2N)_3P=NH \cdot HX$ where each R is, independently, a hydrocarbyl group (alkyl, cycloalkyl, alkenyl, alkynyl, cycloalkenyl, aryl, aralkyl, cycloalkylalkyl, etc.) typically having up to about 30 carbon atoms each, and preferably having up to about 12 carbon atoms each; and X is a halogen atom, e.g., an iodine atom and preferably a chlorine or bromine atom. Compounds in which R is an alkyl group having in the range of 1 to about 6 carbon atoms are preferred. Most preferred is diethylamine.

These compounds can be made by a two-step procedure, the first step of which involves reacting a phosphorus trihalide with a carbon tetrahalide and a dihydrocarbylamine at one or more temperatures in the range of about −10° to about 60° C., and preferably in the range of about 0° to about 30° C. Typically the reactants are mixed in proportions of in the range of about 6 to about 10 moles, and preferably in the range of about 6 to about 8 moles, of the secondary amine and in the range of about 1 to about 500 moles, and preferably in the range of about 1 to about 20 moles, of the carbon tetrahalide per mole of the phosphorus trihalide. In the second step, the reaction product so formed is treated with excess ammonia at one or more temperatures in the range of about 0° to about 100° C., preferably in the range of about 20° to about 60° C., and most preferably in the range of about 30° to about 50° C., whereby the phosphoroamidite is formed. Proportions of about 1 to about 4 moles, and preferably about 1 to about 3 moles, of ammonia per mole of phosphorus product(s) in the reaction product mixture are usually employed.

The reactions involved in these two steps are illustrated by the chemical equations given in the Example hereinafter that depict the particular reactions described therein.

Chemically indifferent organic solvents (i.e., substantially inert solvents or wholly inert solvents) can be used in either such reaction step, if desired. However, in at least cases where the secondary amine is a liquid and where the phosphorus intermediate formed in the first step is a liquid at reaction temperatures, it is not necessary to use a separate solvent. Suitable solvents that can be used when necessary or desirable include benzene, toluene, individual or mixed xylenes, mixed hexanes, n-heptane, petroleum ether or like substantially inert hydrocarbons or mixtures thereof.

Preparation of the tetrakis(dihydrocarbylamino) phosphonium halide involves (a) forming a mixture from (i) a tris(dihydrocarbylamino) phosphoroamidite and/or hydrohalide thereof, (ii) a strong base in proportions of about 2.0 to about 4.0 moles of (ii) per mole of (i), and (iii) at least one solvent for the strong base; (b) mixing a hydrocarbyl monohalide with the mixture formed in (a) in proportions of about 1.0 to about 3.0 moles of hydrocarbyl monohalide per mole of (i) used in forming the mixture of (a); and (c) maintaining the mixture formed in (b) at one or more suitable reaction temperatures at which tetrakis(dihydrocarbylamino) phosphonium halide is produced.

The strong base can be an organic base such as tetramethylammonium chloride, or the like. However use of strong inorganic bases especially oxides and hydroxides of the alkali metals or of calcium, strontium and/or barium or preformed solutions made therefrom are preferred for this use. Preformed solutions in water or in one or more liquid alcohols, or in mixtures of both are suitable, and of these, aqueous solutions are preferred. Although well known to those skilled in the art, it is deemed necessary, or at least prudent, to point out that because the inorganic base is in solution either (i) when used as a preformed solution or (ii) when it comes in contact with the solvent after being charged to the reaction vessel in its original dry form, one or more natural transformations occur. The initial basic substance may be ionized, solvated, or even undergo a chemical reaction with the solvent to form the basic solution. All such natural occurrences are within the comprehension and scope of this disclosure.

The preferred bases are aqueous solutions of sodium hydroxide or of potassium hydroxide or of mixtures thereof, which can be formed, if desired, from adding their respective oxides to water.

It is preferable to add the base or the solution of the base to the phosphoroamidite and/or hydrogen halide complex thereof. However it is possible to mix these substances in other ways such as by feeding them concurrently into a reaction vessel, or by adding the phosphoroamidite to the base or solution thereof. Other ways of bringing these materials together will now be readily apparent from a reading of this description.

After the mixture has been formed from the phosphoroamidite and/or hydrogen halide salt thereof, the strong base, and the solvent for the base, the hydrocarbyl monohalide is mixed therewith. The reactant can be any hydrocarbyl chloride, bromide or iodide (or combination thereof) having up to about 20 carbon atoms, and preferably up to about 12 carbon atoms, in the molecule. The hydrocarbyl group can be of any of the types referred to above relative to R in the above formulas. However use of alkyl monohalides, most especially alkyl monobromides or alkyl monochlorides having up to about 6 carbon atoms in the molecule is preferred. Use of ethyl bromide or ethyl chloride is especially preferred, particularly when the phosphoroamidite used is tris(diethylamino)phosphoroamidite and/or the hydrochloride or hydrobromide thereof, as the product formed therefrom is of great effectiveness as a catalyst in halex reactions.

The reaction to form the tetrakis(dihydrocarbylamino) phosphonium halide pursuant to this invention is typically conducted at one or more temperatures in the range of about 20° to about 90° C. although it is possible to use temperatures outside of this range. Preferred conditions involve use of one or more reaction temperatures in the range of about 50° to about 90° C. The reaction can be conducted in a chemically indifferent solvent whenever this is deemed necessary or desirable. Suitable solvents include benzene, toluene, individual or mixed xylenes, mixtures such as BTX, and the like. Reaction periods typically fall in the range of about 2 to about 30 hours, and preferably in the range of about 4 to about 24 hours.

The practice of this invention is illustrated by the following non-limiting example in which all percentages are by weight.

EXAMPLE

Tris(diethylamino)phosphoroamidite $PCl_3$ (167.3 g, 106.3 mL, 1.22 moles) and $CC_4$ (1554 mL) were placed in a 3-L four-necked flask equipped with an overhead stirrer, a 250 mL dropping funnel, a reflux condenser and a thermocouple. (The system was well purged with nitrogen but all of the reagents were weighed in air).

The vessel was cooled to 5° C. in an ice-bath and the $Et_2NH$ (546.9 g, 773.6 ml, 7.48 moles) added dropwise. The temperature was never allowed to rise above 30° C. during the addition. (The highest temperature observed was 27° C.). The addition took approximately 3.5 hours giving a slightly turbid thick solution.

An ammonia charging bomb was then set-up and attached to the vessel. (A known weight of ammonia had previously been condensed into a stainless steel charging bomb from a lecher bottle). The ammonia (24.83 g, 1.46 moles) was fed through Tygon tubing and into the liquid via a stainless steel needle. The addition took almost 2 hours and the temperature rose to 56° C. A bright yellow slurry was obtained at the end of the addition and the mixture was allowed to stir overnight.

The $Et_2NH·HCl$ was filtered on a medium frit to give an amber solution. The solid was washed with 3×150 mL of $CCl_4$. The volatiles were removed from the combined filtrate and washings on a Rotovap apparatus to give a thick, viscous amber liquid. A $^{31}P\{^1H\}$ nmr showed a clean reaction to the phosphoroamidite.

The reactions involved in this synthesis of tris (diethylamino)phosphoroamidite can be depicted as follows:

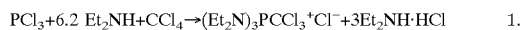

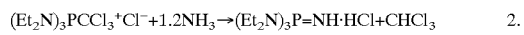

Tetrakis(diethylamino)phosphonium bromide

The above thick, viscous amber liquid was placed in a 2-L flask and treated with 50% aqueous NaOH (195.4 g, 97.7 g, 2.44 moles). The mixture was agitated for approximately 1 hour giving a thick emulsion. The mixture was then treated with 20% NaOH (292.8 g, 58.5 g, 1.46 moles) and EtBr (292.5 g, 2.68 moles). The mixture was heated slowly up to 70° C. and allowed to heat overnight (18 hours). Upon cooling the mixture separated into two phases. The mixture was treated with $CH_2Cl_2$ (200 mL) and the layers separated very easily. The aqueous layer was extracted a second time with $CH_2Cl_2$ and the layers were combined and dried over $Na_2SO_4$. After filtration, the bulk of the volatiles were removed on a Rotovap to give a brown oil. Drying in vacuo at 90° C. gave a pasty solid. The solid was triturated with $Et_2O$ and isolated on a medium frit.

Yield: 292 g (60% from $PCl_3$).

A $^{31}P\{^1H\}$ nmr showed a clean spectrum for the product.

The reactions involved in this synthesis of tetrakis (diethylamino)phosphonium bromide can be depicted as follows:

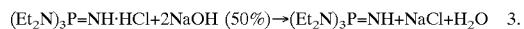

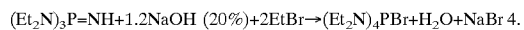

In some Halex processes, it is possible to make use of the above oil/paste without conducting any purification step.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. Thus the fact that a substance, component or ingredient may have lost its original identity through a chemical reaction or transformation during the course of contacting, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof.

The term "substantially" is used in this herein to avoid the possibility of an erroneous assertion that what is being described or claimed refers to an absolute. As those of ordinary skill in chemistry readily understand, absolutes in respect to chemical reactions are the exception rather than the rule; usually small amounts of undesired materials (e.g., impurities) can be tolerated without materially affecting the desired reaction in an adverse manner. Thus the use of the term "substantially" is used herein as a chemist of ordinary skill would understand it, with the application of common sense.

Each and every patent or publication referred to in any portion of this specification is incorporated into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for preparing tetrakis(dihydrocarbylamino) phosphonium halide which comprises:
    a) forming a mixture from (i) at least one tris (dihydrocarbylamino)phosphoroamidite-hydrohalide and (ii) an at least 20 wt % aqueous alkali metal hydroxide solution in proportions in the range of about 2.0 to about 4.0 moles of (ii) per mole of (i), and agitating such mixture for a period of at least 0.5 hour;
    b) mixing together (iii) mixture from a), (iv) a 20 to 50 wt % aqueous alkali metal hydroxide solution, and (v) at least one hydrocarbyl monohalide in proportions in the range of about 2.0 to about 4.0 moles of (iv) per mole of (i) used in forming the mixture of a), and in the range of about 1.0 to about 3.0 moles of (v) per mole of (i) used in forming the mixture of a); and
    c) maintaining the mixture formed in b) at one or more temperatures in the range of about 20° to about 90° C. at which tetrakis(dihydrocarbylamino)phosphonium halide is produced.

2. A process according to claim 1 wherein the tris (dihydrocarbylamino)phosphoroamidite is at least one tris (dialkylamino)phosphoroamidite; wherein the respective aqueous alkali metal hydroxide solutions of a) and of b) each consists essentially of a sodium hydroxide solution or a potassium hydroxide solution, or a sodium hydroxide and potassium hydroxide solution; and wherein the hydrocarbyl monohalide is at least one hydrocarbyl monochloride or at least one hydrocarbyl monobromide, or a combination of at least one hydrocarbyl monochloride and at least one hydrocarbyl monobromide.

3. A process according to claim 1 wherein the tris (dihydrocarbylamino)phosphoroamidite is tris (diethylamino)phosphoroamidite; wherein said respective alkali metal hydroxide solutions both consist essentially of aqueous sodium hydroxide solutions; and wherein the hydrocarbyl monohalide is ethyl bromide.

4. A process according to claim 1 wherein in c) the mixture is heated at one or more temperatures in the range of about 50° to about 90° C.

5. A process according to claim 1 wherein in a) the alkali metal hydroxide solution is added to the tris (dihydrocarbylamino)phosphoroamidite, and wherein in b) the hydrocarbyl monohalide is added portionwise to the mixture formed in a).

6. A process according to claim 5 wherein the tris (dihydrocarbylamino)phosphoroamidite is at least one tris (dialkylamino)phosphoroamidite; wherein said respective aqueous alkali metal hydroxide solutions both consist essentially of an aqueous sodium hydroxide solution or an aqueous potassium hydroxide solution, or an aqueous sodium hydroxide and potassium hydroxide solution; and wherein the hydrocarbyl monohalide is at least one hydrocarbyl monochloride or at least one hydrocarbyl monobromide, or a combination of at least one hydrocarbyl monochloride and at least one hydrocarbyl monobromide.

7. A process according to claim 5 wherein the tris (dihydrocarbylamino)phosphoroamidite is tris (diethylamino)phosphoroamidite; wherein the aqueous alkali metal hydroxide solution consists essentially of an aqueous sodium hydroxide solution; and wherein the hydrocarbyl monohalide is ethyl bromide.

8. A process for preparing tetrakis(dihydrocarbylamino) phosphonium halide which comprises:
    a) mixing together concurrently and/or sequentially and individually and/or in any subcombination thereof, phosphorus trihalide, carbon tetrahalide and dihydrocarbylamine in proportions of about 6 to about 8 moles of the amine and about 1 to about 500 moles of the carbon tetrahalide per mole of the phosphorus trihalide, and maintaining the mixture at one or more reaction temperatures in the range of about −10° to about 60° C. to produce a first reaction mixture;
    b) contacting at least a portion of the first reaction mixture with excess ammonia at one or more temperatures in the range of about 0° to about 100° C. such that tris(dihydrocarbylamino) phosphoroamidite is formed;
    c) mixing together concurrently and/or sequentially and individually and/or in any subcombination thereof (i) at least a portion of tris(dihydrocarbylamino) phosphoroamidite from b), (ii) at least one strong base in proportions of about 2.0 to about 4.0 moles of base per mole of phosphoroamidite, and (iii) at least one solvent for said base;
    d) mixing with at least a portion of the mixture formed in c), at least one hydrocarbyl monohalide in proportions of about 1.0 to about 3.0 moles of hydrocarbyl monohalide per mole of phosphorus trihalide used in forming the mixture of a); and
    e) maintaining the mixture formed in d) at one or more temperatures at which tetrakis(dihydrocarbylamino) phosphonium halide is produced;
the halogen atoms of all of the aforementioned halides being other than fluorine atoms.

9. A process according to claim 8 wherein the phosphorus trihalide is phosphorus trichloride, wherein the carbon tetrahalide is carbon tetrachloride in an amount of about 1 to about 20 moles per mole of the phosphorus trichloride, wherein the dihydrocarbylamine is a dialkylamine, wherein the strong base is an oxide or hydroxide of at least one alkali metal and/or of at least one alkaline earth metal of atomic number above 12, wherein the solvent for the base is water, or an alcohol, or a mixture thereof, and wherein the hydrocarbyl monohalide is an alkyl chloride or alkyl bromide.

10. A process according to claim 9 wherein the strong base is an oxide or hydroxide of at least one alkali metal, and wherein the solvent for the base is water.

11. A process according to claim 10 wherein the dialkylamine is diethyl amine; and wherein the strong base is a preformed aqueous sodium hydroxide solution, a preformed aqueous potassium hydroxide solution or a preformed aqueous sodium hydroxide and potassium hydroxide solution, said solution being preformed from the oxide or hydroxide of sodium and/or potassium and at least a portion of said solvent.

12. A process according to any of claims 1, 5, and 6 taken individually wherein a), b) and c) are conducted in the same reactor.

13. A process according to any of claims 8, 9, and 11 taken individually wherein c), d) and e) are conducted in the same reactor.

* * * * *